(12) United States Patent
Koehler

(10) Patent No.: US 8,986,281 B2
(45) Date of Patent: Mar. 24, 2015

(54) ANTI-THROMBOGENIC CATHETER AND METHOD

(71) Applicant: Cleve S Koehler, Ellettsville, IN (US)

(72) Inventor: Cleve S Koehler, Ellettsville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 89 days.

(21) Appl. No.: 13/720,203

(22) Filed: Dec. 19, 2012

(65) Prior Publication Data

US 2013/0110083 A1 May 2, 2013

Related U.S. Application Data

(62) Division of application No. 12/333,940, filed on Dec. 12, 2008, now abandoned.

(60) Provisional application No. 61/016,753, filed on Dec. 26, 2007.

(51) Int. Cl.
| | |
|---|---|
| *A61M 31/00* | (2006.01) |
| *A61M 25/00* | (2006.01) |
| *A61M 25/06* | (2006.01) |

(52) U.S. Cl.
CPC ....... *A61M 25/0026* (2013.01); *A61M 25/0017* (2013.01); *A61M 25/0023* (2013.01); *A61M 25/003* (2013.01); *A61M 25/0045* (2013.01); *A61M 25/007* (2013.01); *A61M 2025/004* (2013.01); *A61M 2025/0681* (2013.01)
USPC .......................... 604/508; 604/43; 604/164.08

(58) Field of Classification Search
CPC .......... A61M 25/007; A61M 25/0026; A61M 2025/0034; A61M 2025/0681; A61M 2210/125; A61B 2017/00243
USPC ...................... 604/508, 171, 164.02
See application file for complete search history.

(56) References Cited

U.S. PATENT DOCUMENTS

| | | | |
|---|---|---|---|
| 4,995,865 A | 2/1991 | Gahara et al. | |
| 5,425,723 A | 6/1995 | Wang | |
| 5,738,649 A | 4/1998 | Macoviak | |
| 5,797,869 A | 8/1998 | Martin et al. | |
| 6,808,510 B1 * | 10/2004 | DiFiore | 604/171 |
| RE39,451 E * | 12/2006 | Kuhle | 604/6.16 |

OTHER PUBLICATIONS

U.S. Appl. No. 12/333,940, filed Dec. 12, 2008, Koehler.

* cited by examiner

*Primary Examiner* — Kevin C Sirmons
*Assistant Examiner* — Deanna K Hall
(74) *Attorney, Agent, or Firm* — Brinks Gilson & Lione

(57) ABSTRACT

A medical catheter assembly is provided including an inner catheter member, where that inner catheter member includes a plurality of inner catheter lumens, and an outer sheath with at least one patent sheath lumen. The inner catheter is slidably disposed through a length of the at least one patent sheath lumen in a manner providing a substantially sealing contact between an exterior surface of the inner catheter and an inward surface of the at least one patent sheath lumen. A first of the plurality of inner catheter lumens includes a plurality of apertures to the exterior surface of the inner catheter, and a second of the plurality of inner catheter lumens includes at least one distal end-tip opening. A method of using the assembly is also provided.

17 Claims, 3 Drawing Sheets

ANTI-THROMBOGENIC CATHETER AND METHOD

RELATED APPLICATIONS

This application is a divisional application of U.S. application Ser. No. 12/333,940, filed on Dec. 12, 2008, pending, which claims the benefit of U.S. Provisional Application No. 61/016,753, filed on Dec. 26, 2007, the entireties of which are herein incorporated by reference.

FIELD OF THE INVENTION

The present invention relates generally to medical catheter devices and more particularly to indwelling catheters and methods related to same.

BACKGROUND

An indwelling catheter (e.g., central venous catheter) commonly is placed into a central blood vessel of a patient undergoing medical treatment for prolonged, long-term, or chronic conditions. The catheter provides for infusion of therapeutic materials such as, for example, chemotherapy agents. The presence of an indwelling catheter often increases the risk of deep vein thrombosis (DVT), which is the formation of a blood clot (thrombus) in a deep vein. Although the causes of DVT are not well understood, it may occur as a result of turbulence or other disruption in blood flow caused by the catheter. The blood clot may become dislodged (at which time it is termed an embolus) and move through venous circulation to another location in the body. This is particularly serious if the embolus is transported through venous circulation to, and through, the heart, where it can become lodged with and block a pulmonary artery. This blockage of blood flow to a region of the lungs can cause permanent lung damage or death. If the embolus lodges elsewhere in the body, for example where it impedes or blocks blood flow in a muscle of an extremity, it can cause extreme pain and permanent tissue damage.

In many patient populations, so-called blood-thinners (e.g., warfarin, heparin) are introduced systemically when an indwelling catheter is present in order to decrease the risk of DVT. However, there are significant potential side effects from such treatment including increased risk of bleeding and hemorrhage. These risks may be even greater for patients suffering from conditions where use of an indwelling catheter is indicated.

Pediatric patients are often at risk of DVT in conjunction with an indwelling catheter. However, the risk of DVT in pediatric patients is generally low enough that the risk of side effects from use of blood-thinners outweighs the risk of embolus formation and blood-thinners are not used as commonly as in, for example, geriatric patients. The risk-balancing calculus associated with these facts must also take into account that DVT is considered more serious in pediatric patients because they have the opportunity to live an entire life span of 60-80 years after a pediatric DVT incident, and the damage done by an embolus can have crippling long term effects on development and quality of life. Of course, improved long-term quality of life and reduced risk of DVT is important for patients of any age.

For this reason, it is desirable to provide an indwelling catheter and method of use that may reduce the risk of DVT associated with use of an indwelling catheter. One such approach has used heparin impregnated in polymers of a catheter itself or applied to its surface. This approach is useful, but there may also be a need for adjustable control or user-selectable location-targeting of an anti-DVT agent, which may also be desirable to provide treatment tailored for individual patients based upon age and other specific indications for treatment.

BRIEF SUMMARY

In one aspect, a medical catheter assembly may include an inner catheter member, where the inner catheter member includes a plurality of inner catheter lumens, and an outer sheath with at least one patent sheath lumen. The inner catheter may be slidably disposed through a length of the at least one patent sheath lumen in a manner providing a substantially sealing contact between an exterior surface of the inner catheter and an inward surface of the at least one patent sheath lumen. A first of the plurality of inner catheter lumens may include a plurality of apertures to the exterior surface of the inner catheter, and a second of the plurality of inner catheter lumens may include at least one distal end-tip opening.

In another aspect, a medical catheter assembly may be configured for use as an indwelling central venous catheter and include an elongate inner catheter body and an outer sheath. The elongate inner catheter body may include a central first lumen including a distal end-tip opening, an outer second lumen, and a plurality of apertures open from the outer second lumen to an exterior surface of the elongate inner catheter body. The outer sheath may include a sheath lumen through which at least a portion of the elongate inner catheter body is slidably disposed, wherein a surface of the sheath lumen sealingly contacts the exterior surface of the elongate catheter body such that fluid communication through any of the plurality of apertures is substantially prevented for apertures covered by the outer sheath.

In another aspect, a method for installing a catheter may include the steps of: providing a catheter assembly as described herein, directing the assembly into proximity with a blood vessel, further directing the inner catheter member through a wall of the blood vessel and into a vessel lumen thereof, and further directing the outer sheath into close proximity with the blood vessel such that substantially none of the plurality of inner catheter apertures are open outside the blood vessel, said inner catheter apertures being open into the vessel lumen or sealingly covered by the outer sheath, directing a first therapeutic agent though the first inner catheter lumen and at least one inner catheter aperture, and directing a second therapeutic agent through the second inner catheter lumen.

DETAILED DESCRIPTION OF THE DRAWINGS AND THE PRESENTLY PREFERRED EMBODIMENTS

Figure 1:
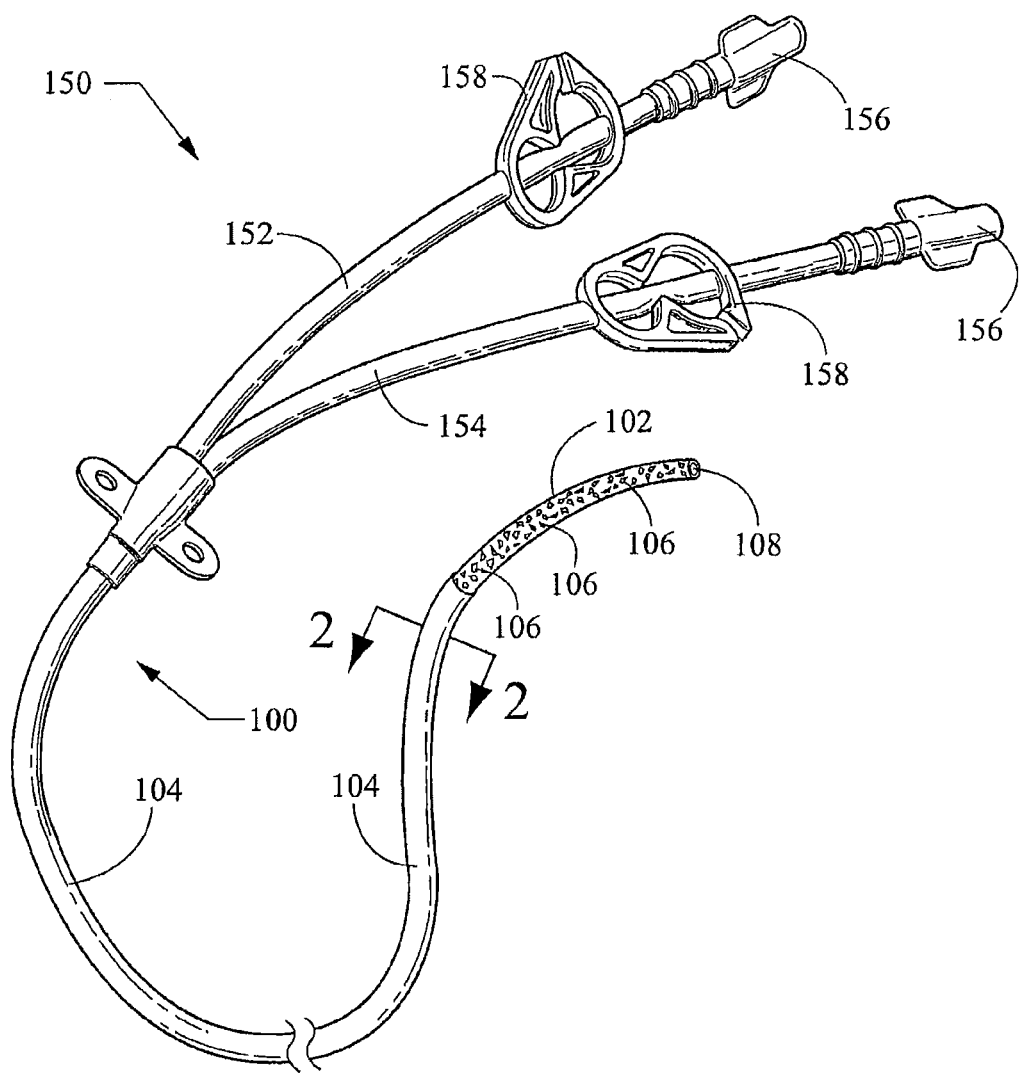
FIG. 1 shows a first embodiment of a catheter assembly.

FIG. 1 shows one embodiment of a medical catheter assembly 100. The catheter assembly 100 includes an inner catheter member 102 and an outer sheath 104. The inner catheter 102 is slidably disposed through a lumen of the outer sheath 104 so that it can be withdrawn into and extended out from it. The slidable relationship includes providing a substantially sealing contact between the exterior surface of the inner catheter 102 and an inward surface of the lumen of the outer sheath 104, which preferably is fluid-patent (i.e., fluid is prevented from traveling out of any apertures covered by the sheath). The outer sheath 104 may also have other lumens, which may or may not be fluid-patent including, for example, a wire guide lumen.

The inner catheter 102 includes a plurality of apertures 106 along its external surface and a distal end-tip opening 108. In the embodiment shown in FIG. 1, the distal end is slightly tapered so as to be rounded, but those of skill in the art will appreciate that the distal end may be more or less gradually tapered, blunt, or incorporating some other geometry, all within the scope of the present invention.

Figure 2:
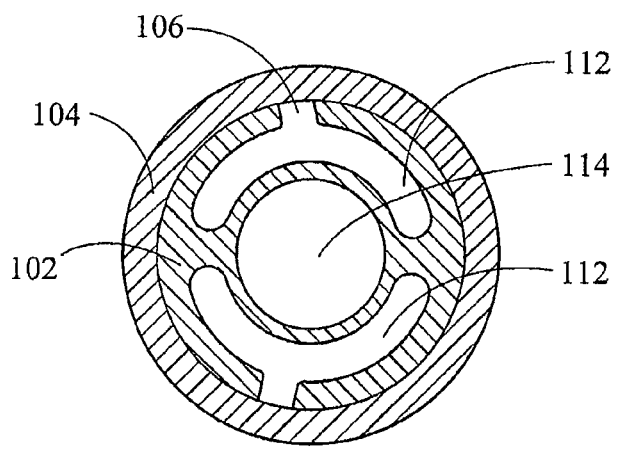
FIG. 2 shows a transverse cross-sectional view of the catheter assembly of FIG. 1 taken along line 2-2.

FIG. 2 shows a magnified transverse section view along line 2-2 of FIG. 1. As shown in FIG. 2, the inner catheter 102 includes an outer first lumen 112 and a second central lumen 114. The apertures 106 shown in FIGS. 1 and 2 provide external fluid communication for the outer lumen 112 so that fluid can exit the outer lumen through any apertures 106 that are not covered by the outer sheath 104. In one embodiment, more distal apertures 106 may be larger than more proximal apertures 106 in a manner that may provide consistent fluid flow therethrough along the inner catheter length as fluid pressure may change as some fluid is released through more proximal apertures. In various embodiments, the size of apertures along the catheter length may be made larger or smaller to vary/control flow rate in a desired manner along predetermined regions of the catheter length. FIG. 2 includes two outer lumens 112 that are generally symmetrical to each other and that may be open to (i.e., in fluid communication with) each other. Other embodiments may include one outer lumen open to the apertures 106 or a plurality of two or more outer lumens, which may be symmetric or asymmetric in cross-section and relative to each other.

It is preferable that the apertures 106 be generally uniformly distributed around the outer circumference of the inner catheter 102, but some embodiments may have asymmetrically/nonuniformly distributed apertures. Specifically, a greater or lesser density of apertures 106 may be provided more proximally, centrally, or distally along the portion of the inner catheter 102 having those apertures, and/or the apertures may be uniformly or non-uniformly distributed around the catheter circumference. In preferred embodiments, the apertures 106 will be dimensioned to allow efficient low-level flow of an anti-clotting agent in a concentration effective to decrease risk of thrombus formation in the region of the catheter assembly. For example, the diameter of circular apertures may be about 0.1 mm to about 1 mm, with a diameter range of about 0.3 mm to about 0.5 mm in certain embodiments. The apertures may be circular, obround, oval, elliptical, polygonal or any other shape effective to release the desired compound. It is preferable that the dimensions and geometry of the apertures provide for sufficiently low-level flow that a minimum effective concentration of the anti-clotting agent is used for the purpose of minimizing potential undesired side effects. As another example, more proximal apertures may have a different shape and/or different surface area than more distal apertures (see, e.g., FIG. 3). In some embodiments, the catheter assembly may be dimensioned for use in treatment of pediatric patients. Preferred embodiments will be constructed of biocompatible polymers such as, for example, ePTFE, polyurethane, silicone, or other polymers, preferably including polymers having a low-friction surface.

In certain embodiments, an anti-thrombogenic/anti-clotting agent such as, for example, heparin, may be bonded to the exterior of the inner catheter and/or the sheath (see, e.g., U.S. Publ. Pat. App. 2005/0100580, Cook, Inc., Bloomington, Ind., which is incorporated herein by reference in its entirety).

The inner lumen 114 and its distal opening 108 preferably are dimensioned to provide for effective introduction to a patient of a therapeutic material such as, for example, nutrient fluids, chemotherapeutic agents, therapeutic drugs, whole blood, blood plasma, and/or other materials.

FIG. 1 also shows one example of a proximal structure, embodied as a dual-catheter hub structure 150, that may be used to provide a user interface with the device 100. The hub structure 150 includes a proximal first catheter 152 and a proximal second catheter 154. Each of the catheters 152, 154 includes a connection hub 156 (such as, for example, a luer-type hub or other fluid-tight access means that preferably provides for quick, easy connection/disconnection) at its proximal end. The proximal first catheter 152 provides a patent lumen in fluid communication with the outer first lumens 112 of the inner catheter 102. The proximal second catheter 154 provides a patent lumen in fluid communication with the inner second lumen 114 of the inner catheter 102. In one preferred embodiment, one or both of the proximal catheters will include visual and/or tactile indicia for a user readily to distinguish them from each other (such as, for example, banding, color coding, text labeling, differing sizes, differing geometric shapes, etc., or any combination thereof). The proximal structure may also include clips (such as, for example, the clips 158, or any other clip configuration). Those of skill in the art will appreciate that other configurations of the proximal structure used in existing indwelling catheter devices and other devices, as well as configurations presently known or developed in the future, may be used within the scope of the present invention.

Figure 3:
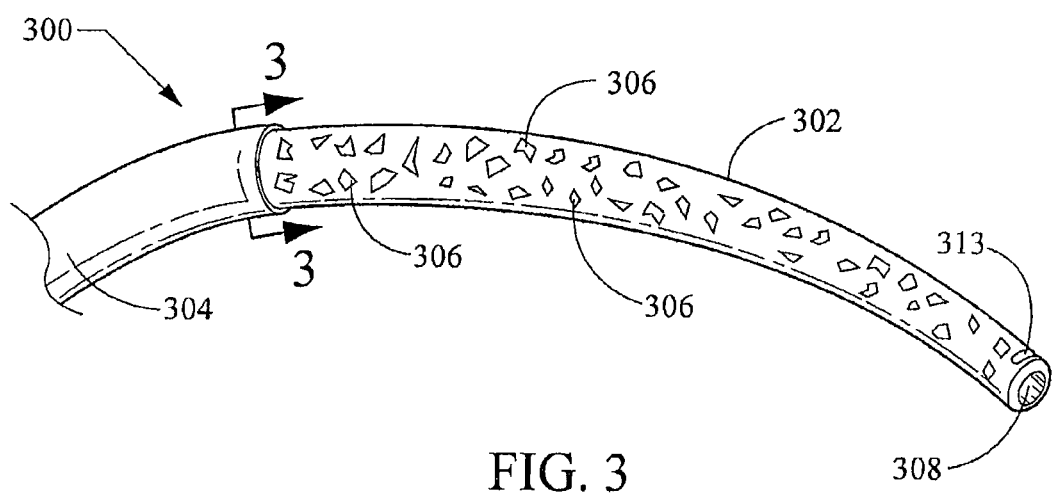
FIG. 3 shows a second embodiment of a catheter assembly.

FIG. 3 shows another embodiment of a medical catheter assembly 300. The catheter assembly 300 includes an inner catheter member 302 and an outer sheath 304. The inner catheter 302 is slidably disposed through a lumen of the outer sheath 304 so that it can be withdrawn into and extended out from it. The slidable relationship includes providing a substantially sealing contact between the exterior surface of the inner catheter 302 and an inward surface of the lumen of the outer sheath 304, which preferably is fluid-patent (i.e., fluid is prevented from traveling out of any apertures covered by the sheath). The outer sheath 304 may also have other lumens, which may or may not be fluid-patent including, for example, a wire guide lumen.

The inner catheter 302 includes a plurality of apertures 306 along its external surface and a distal end-tip opening 308. In the embodiment shown in FIG. 3, the distal end is slightly tapered so as to be at least slightly rounded (presenting an atraumatic distal profile), but those of skill in the art will appreciate that the distal end may be more or less gradually tapered, blunt, or incorporating some other geometry, all within the scope of the present invention.

The apertures 306 shown in FIG. 3 provide external fluid communication for the outer lumens so that fluid can exit the outer lumen through any of the outer lumen apertures 306 that are not covered by the outer sheath 304. In one embodiment, more distal apertures 306 may be larger than more proximal apertures 306 in a manner that may provide consistent fluid flow therethrough along the inner catheter length as fluid pressure may change as some fluid is released through more proximal apertures.

Figure 3A:
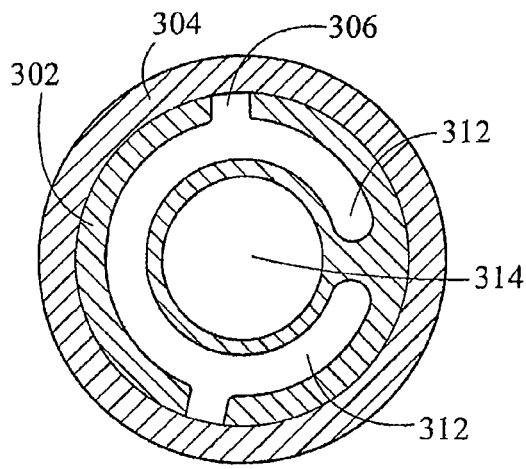
FIGS. 3A, 3B, and 3C show, respectively, alternative transverse cross-sectional views (taken along line 3-3) of different embodiments of the catheter assembly shown in FIG. 3.
Figure 3B:
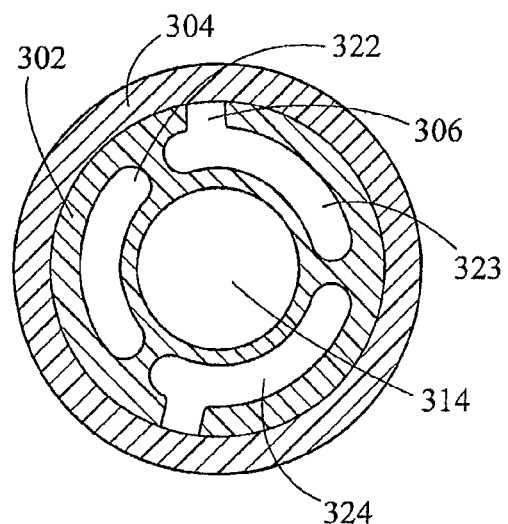
Figure 3C:
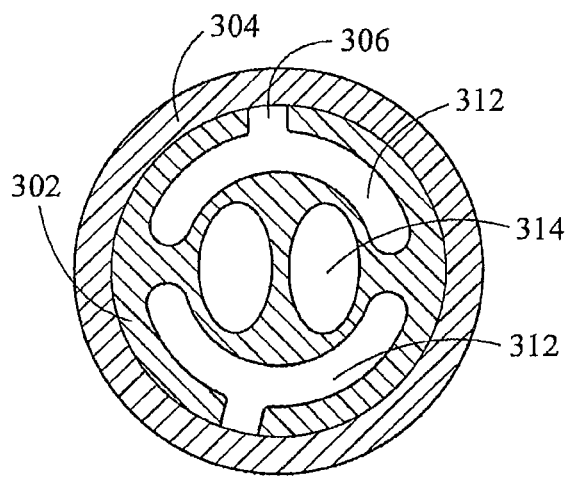

FIGS. 3A, 3B, and 3C represent different possible embodiments of the catheter assembly 300, shown in cross-section views taken along line 3-3 of FIG. 3. In FIG. 3A, the inner catheter 302 includes a single outer first lumen 312 and a central second lumen 314.

In the embodiment shown in FIG. 3B, the inner catheter 302 includes three outer first lumens 322, 323, 324 and a central lumen 314. Those of skill in the art will appreciate that one or more of the outer first lumens may not include any side apertures, but may include one or more distal end-tip openings. The tapered distal end of the inner catheter 302 includes a distal aperture 313 providing fluid communication from the outer first lumen 322. Such an embodiment will provide a patent path that may be used, for example, for passage of a wire guide, introduction of a radio-opaque contrast fluid, introduction of another therapeutic material in addition to (either simultaneously with, or at a different time than) the first therapeutic material being introduced through the central lumen, or other application. However, within the scope of the present invention, at least one of the outer lumens will include a plurality of distal apertures providing fluid communication from one of the outer lumens to the exterior of the inner catheter, but sealable by being covered by the outer sheath.

FIG. 3C shows a transverse section view of dual-lumen embodiment. The inner catheter includes two inner lumens 314 and two outer lumens 312. The outer lumens 312 preferably include one or more apertures 306. The dual inner lumens 314 may be used for different or similar purposes relative to each other in one or more manners, including as described above.

Those of skill in the art will appreciate that the embodiments described above may have multiple applications. One preferred use will include configuration for placement as a central venous catheter and effective delivery of a therapeutic agent through the central lumen, while providing a low dosage of an anti-thrombogenic agent (e.g., an anti-coagulant such as, for example, warfarin or heparin). The low dosage preferably will be a minimum level effective to prevent thrombus formation in the vicinity of, and/or related to the presence of, the catheter assembly in the patient. In some embodiments, the apertures permitting delivery of anti-thrombogenic agent(s) from the outer lumen(s) may be configured for uni-directional flow, and/or may be configured to minimize the likelihood of—or even prevent—entry of a significant blood volume into the outer lumen(s). Means for providing these features are known in the art including, for example, providing a low-flow pucker-type valve formed in one or more of the apertures and/or providing apertures that are sufficiently small to allow passage of a low-viscosity solution of anti-thrombogenic agent, but not to allow easy passage of a more viscous and/or particulate-containing fluid such as blood. As is described below with reference to methods of the present invention, embodiments of a catheter assembly of the present invention may permit location-targeting for delivery of anti-thrombogenic agents.

A method of use is discussed here with reference to the catheter assembly 100 illustrated in FIGS. 1-2. In a method for installing a catheter, the catheter assembly 100 is directed in a patient body to a location adjacent a blood vessel (such as, for example, a jugular vein, subclavian vein, brachial vein, basilica vein, or femoral vein). The inner catheter 102 may then be extended out of the distal sheath end and directed into the lumen of the blood vessel. During installation, the catheter assembly 100 may configured with the inner catheter 102 withdrawn into the sheath 104, preferably such that the distal ends thereof are generally aligned. In some embodiments, the sheath 104 may include or be directed through a penetrating member (such as, for example, a needle—not shown) to facilitate directing the assembly 100 to the blood vessel.

The sheath 104 may remain outside the blood vessel with its distal end adjacent thereto. Preferably, this configuration will expose only the inner catheter apertures 106 that are within the blood vessel lumen, which will prevent the loss of anti-thrombogenic agent therethrough into the space around the blood vessel. More importantly, this feature allows use of a single catheter assembly design, the length of which can selectably be configured for different patients based upon size and anatomy, and/or to target delivery of one or more therapeutic materials. As one example of an advantage presented by the present design, dosage quantity of the anti-clotting agent may be controlled in part by adjusting the length of the catheter portion with exposed apertures in the blood vessel. As another example, the length to be extended in a patient blood vessel can also be controlled. This is in contrast with other indwelling catheter designs that commonly are available in predetermined sizes that do not allow the flexibility of placement permitted with the present design, a feature that will be evident to those of skill in the art from the method described above.

In another alternative method (not shown), the sheath and inner catheter may both be introduced into a blood vessel or other body lumen. Thereafter, the number of exposed apertures (and resulting flow/concentration of an agent being introduced therethrough) may be modulated by the distance to which the inner catheter is extended out of the distal end of the outer sheath.

The figures illustrating the device embodiments described above are not intended to be to scale, and should not be construed as limiting with regard to any dimension, proportion, or combination. Those of skill in the art will appreciate that many embodiments not described herein may be practiced within the scope of the present invention. It is therefore intended that the foregoing detailed description be regarded as illustrative rather than limiting, and that it be understood that the following claims, including all equivalents, are intended to define the spirit and scope of this invention.

The invention claimed is:

1. A method for installing a catheter assembly having an inner catheter member comprising a plurality of inner catheter lumens, and an outer sheath comprising at least one patent sheath lumen; where the inner catheter is slidably disposed through a length of the at least one patent sheath lumen in a manner providing a substantially sealing contact between an exterior surface of the inner catheter and an inward surface of the at least one patent sheath lumen; a first of the plurality of inner catheter lumens comprising a plurality of apertures to the exterior surface of the inner catheter; and a second of the plurality of inner catheter lumens comprising at least one distal end-tip opening; the method comprising the steps of:

directing the catheter assembly into proximity with a blood vessel;

further directing the inner catheter member through a wall of the blood vessel into a vessel lumen thereof, and further directing the outer sheath into close proximity with the blood vessel such that substantially none of the plurality of inner catheter apertures are open outside the blood vessel, said inner catheter apertures being open into the vessel lumen or sealingly covered by the outer sheath;

directing a first therapeutic agent through the first inner catheter lumen and at least one inner catheter aperture; and, directing a second therapeutic agent through the second inner catheter lumen;

wherein the plurality of apertures comprises at least four apertures, the apertures being distributed around a circumference and along a length of the inner catheter;

wherein a more distal aperture of the plurality of apertures comprises a larger surface area than a surface area of a more proximal aperture such that the flow of the first therapeutic agent through the more distal aperture and the more proximal aperture is the same when the more distal aperture and the more proximal aperture are open into the vessel lumen; and, wherein the plurality of apertures open into the vessel lumen provide for a low-level flow of the first therapeutic agent to deliver a minimum effective concentration of the first therapeutic agent to the exterior surface of the inner catheter.

2. The method of claim 1 further comprising a step of aligning distal ends of the inner catheter member and the outer sheath.

3. The method of claim 1 further comprising a step of directing a distal portion of the outer sheath into the blood vessel.

4. The method of claim 3 further comprising a step of longitudinally adjusting the position of the inner catheter relative to the outer sheath in a manner controlling the number of apertures not covered by the outer sheath.

5. The method of claim 1, wherein the catheter is dimensioned for use as a central venous catheter, and the blood vessel is selected from one of a subclavian vein, a femoral vein, and a jugular vein.

6. The method of claim 1, wherein at least one of the therapeutic agents is an anti-thrombotic agent.

7. The method of claim 1, wherein each of a first sub-plurality of the apertures comprises a different surface area than each of a second sub-plurality of the apertures.

8. The method of claim 1, the catheter assembly further comprising a closed distal end-tip of the first of the plurality of inner catheter lumens such that the plurality of apertures is disposed only along lateral sides of the inner catheter, configured thereby to be sealingly covered by an inward surface of the at least one patent sheath lumen.

9. The method of claim 1, wherein the plurality of apertures comprises at least ten apertures.

10. The method of claim 1, wherein the plurality of apertures comprises at least twenty five apertures.

11. The method of claim 1, wherein each aperture of the plurality of apertures has a diameter between 0.1 mm to 1.0 mm.

12. The method of claim 1, wherein each aperture of the plurality of apertures has a diameter between 0.3 mm to 0.5 mm.

13. The method of claim 1, wherein the plurality of apertures are uniformly distributed around the circumference and along the length of the inner catheter.

14. The method of claim 1, wherein the plurality of apertures are non-uniformly distributed around the circumference and along the length of the inner catheter.

15. The method of claim 1, wherein a flow of the first therapeutic agent through the plurality of apertures open into the vessel lumen is consistent along a length of the inner catheter having the plurality of apertures open into the vessel lumen.

16. The method of claim 1, wherein the plurality of apertures are distributed along a length of at least 3 cm of the inner catheter.

17. The method of claim 1, wherein the plurality of apertures are distributed along a length of at least 6 cm of the inner catheter.

* * * * *